United States Patent [19]

Ramirez et al.

[11] Patent Number: 5,254,334

[45] Date of Patent: Oct. 19, 1993

[54] ANHYDROUS FOAMING COMPOSITION CONTAINING LOW CONCENTRATIONS OF DETERGENTS AND HIGH LEVELS OF GLYCERIN AMD EMOLLIENTS SUCH AS OILS AND ESTERS

[75] Inventors: Jose E. Ramirez, Trumbull; Mohan Vishnupad, Monroe, both of Conn.

[73] Assignee: Imaginative Research Associates, Inc., Bridgeport, Conn.

[21] Appl. No.: 878,363

[22] Filed: May 4, 1992

[51] Int. Cl.$^5$ .................. A61K 7/06; A61K 7/075
[52] U.S. Cl. ...................... 424/70; 514/846; 514/975; 252/162; 252/550; 252/DIG. 5
[58] Field of Search ............... 424/70; 514/846, 975; 252/DIG. 13, DIG. 14, 550, 162, DIG. 5

[56] References Cited

U.S. PATENT DOCUMENTS

| | | | |
|---|---|---|---|
| 3,224,976 | 12/1965 | Farrar et al. | |
| 3,829,563 | 8/1974 | Barry | 514/846 |
| 4,707,293 | 11/1987 | Ferro | 514/846 |
| 4,808,322 | 2/1989 | McLaughlin | 514/846 |
| 4,829,092 | 5/1989 | Nelson | 514/846 |
| 4,931,204 | 5/1990 | Ramirez | 252/DIG. 5 |

FOREIGN PATENT DOCUMENTS 1290689 9/1986 Canada .
460839 2/1937 United Kingdom .

OTHER PUBLICATIONS

Chem. Abstracts, 98160V (1969), Superfatted soaps.
Chem. Abstracts, 5913f (1964), Toilet Bar Soap.
Chem. Abstracts, 95:45134Z, Mar-resistant soap Bar.
Chem. Abstracts, 20850f, Detergent and spot removing composition.
Chem. Abstracts, 5747h, Metallic Soap Petrolatum ointment bases.
Chem. Abstracts, Brit., 29, 113; Dec. 13, 1909.
Catalog; Macalaster Bicknell Co., New Haven, CT (1988).
Seidenfaden and Iberica, *The Use of sarcosides and isethionatyes in cosmetics,* Jul. 1966.

*Primary Examiner*—Thurman K. Page
*Assistant Examiner*—Sally Gardner
*Attorney, Agent, or Firm*—Peter G. Dilworth; Rocco S. Barrese

[57] ABSTRACT

Cosmetically elegant creams contain high levels of glycerine and emollients, sodium cocoyl isethionate at levels of 19% or less and sodium lauryl sulfate at a level of 1 to 5 percent.

13 Claims, No Drawings

5,254,334

ANHYDROUS FOAMING COMPOSITION CONTAINING LOW CONCENTRATIONS OF DETERGENTS AND HIGH LEVELS OF GLYCERIN AMD EMOLLIENTS SUCH AS OILS AND ESTERS

FIELD OF THE INVENTION

This invention relates generally to formulations of anhydrous, cosmetically elegant creams having a high glycerin content and containing sodium cocoyl isethionate in combination with sodium lauryl sulfate to give the creams a desirable consistency.

More particularly, this invention is concerned with the discovery that low levels of sodium cocoyl isethionate and sodium lauryl sulfate in combination with high concentrations of glycerin and high levels of emollients (petrolatum, mineral oils and esters) can be formulated into anhydrous, cosmetically elegant foaming cream.

The unique feature of such composition is that the low levels of detergent and high level of glycerin and emollients provide the maximum functional benefits to skin by providing good foam without any defatting of the skin.

A novel finding of these compositions is the effect of sodium lauryl sulfate in producing the soft, easily processible cream. Sodium lauryl sulfate in a level of one to five percent by weight in the presence of sodium cocoyl isethionate, glycerin and emollients tends to soften the cream significantly. The optimum softening effect is observed at a sodium lauryl sulfate content of about three percent by weight.

BACKGROUND OF THE INVENTION

Prior to the present invention, it was known from Canadian Patent Number 1,290,689 entitled High Oil Containing Anhydrous Foamable Composition, that high levels of petrolatum in mineral oil in combination with high levels of detergents, such as sodium cocoyl isethionate, overcomes the foam suppressing properties of the oil so as to provide an extremely functional, stable, good foaming in cosmetically attractive products.

The prior anhydrous foam oil systems require a high level of petrolatum and mineral oil in the range of 30 to 50 percent by weight, detergent sodium cocoyl isethionate in the level of 20 to 80 percent by weight and additives, such as glycerine, in the level of 0 to 10 percent by weight.

The present invention differs from the above composition in that we find high levels of glycerin in the range of 40 to 60 percent with oils and esters of petrolatum consistency in the range of 10 to 40 percent, sodium cocoyl isethionate at 10 to 19 percent and sodium lauryl sulfate in the range of 1 to 5 percent, provide an extremely functional, good consistency, foaming cleanser which is cosmetically elegant.

Another important discovery in our compositions is the effect of sodium lauryl sulfate on the consistency of the anhydrous foaming cream. Sodium lauryl sulfate at a level of 1 to 5 percent softens the cream consistency significantly with an optimum softening effect seen at the 3 percent level. This softening effect of sodium lauryl sulfate in the high level of glycerin, oils and esters of petrolatum consistency with low level of sodium cocoyl isethionate, permits the production of the cosmetically acceptable, soft creams. The processing of such soft creams is much easier during the manufacturing of such products.

SUMMARY OF THE INVENTION

The present invention combines detergents, such as sodium cocoyl isethionate, at levels of 19 percent or less and sodium lauryl sulfate at a level of 1 to 5 percent with high concentrations of glycerin and emollients, such as oils and esters of petrolatum consistency so as to form highly useful anhydrous composition capable of foaming when combined with water during use.

Preferably the anhydrous cream composition of the present invention comprise:
 a) glycerin in the amount from about 40 to about 60 percent by weight based on the total weight of the composition;
 b) emollients in an amount from about 10 to about 40 percent by weight based on the weight of the total composition;
 c) sodium cocoyl isethionate in an amount from about 10 to about 12 percent by weight based on the weight of the total composition; and
 d) sodium lauryl sulfate in an amount from about 1 to about 5 percent by weight based on the weight of the total composition.

In the case of oils and esters, small amounts of microcrystalline waxes may also be added.

In addition, the anhydrous foaming creams of the present invention may have incorporated therein one or more active ingredients for delivery to the skin during use.

DETAILED DESCRIPTION OF THE INVENTION

The compositions of the present invention contain glycerine in an amount of from about 40 to about 60 percent by weight; sodium cocoyl isethionate in an amount of less than 19 percent by weight; sodium lauryl sulfate in an amount from about 1 to about 5 percent by weight. Preferably, the ratio of sodium lauryl sulfate to sodium cocoyl isethionate is in the range of about 1:3 to about 1:6.

Emollients suitable for use in the compositions of the present invention include petrolatum, mineral oils, and esters such as, for example, isopropyl myristate, isopropyl palmitate and $C_{12}$-$C_{15}$ alcohol benzoates. In the case of oils and esters, a small amount of microcrystalline wax may be added to produce a cosmetically acceptable cream. Typically, microcrystalline wax will be present in an amount from about 4 to about 10 percent by weight.

In addition to the foregoing components, foam boosters may be incorporated into the compositions of the present invention. Suitable foam enhancers include potassium polymetaphosphate, n-pentane, isopentane, sodium lauryl sulfoacetate, amides and sarcosynates. These materials will enhance the foam produced when the present anhydrous cream compositions are exposed to water during use.

The compositions of this invention may also contain additives such as fragrance, color, and gums, such as, for example xanthan gum, to improve the texture, appearance and user perception of the cream. Additionally, active ingredients may be incorporated in the present compositions. Such active ingredients include, but are not limited to deodorants, medicaments such as, for example coal-tar, benzoyl peroxide, vitamin A and vitamin E, and antibacterial ingredients such as, for example, triclosan, PVP-iodine and salicylic acid.

While the cream compositions of this invention are described as anhydrous, it should be understood that a certain amount of water of hydration associated with the various components may be contained in the compostion. Typically, this water of hydration will be less than five percent by weight.

The compositions of the present invention may be prepared by vigorously mixing the ingredients together. The order of addition is not critical. Preferably, and in the Examples which follow, the compositions were prepared as follows: Sodium cocoyl isethionate was added to glycerine heated to 80° C. The mixture was homogenized once the detergent flakes had melted into the glycerine. Sodium lauryl sulfate was added, with continued homogenizing, to the detergent/glycerine phase followed by addition of the oil phase which had been heated to 80° C. Fragrance was added to the composition after the white cream had cooled somewhat.

The consistency of the cream produced was tested after overnight storage of the cream at ambient temperature using a Penetrometer (Penetrometer, Universal, ASTM, (Precision 73510), Catalog No. 33541, Macalaster Bicknell Company of Connecticut, Inc., New Haven, Conn.) which was equipped with a 25 gram cone. The amount of penetration of the cone into the sample was displayed by, and read off of the pentrometer in units of mm×10. A lower penetration value indicates a harder cream. Preferably, the creams of this invention have a penetration value greater than about 130 mm×10.

EXAMPLES 1 TO 10

The compositions of Examples 1 to 10 show the effect that changing the amount of sodium lauryl sulfate in the composition has on the consistency of the anhydrous cream.

In examples 1 to 4, the formulations of which are presented in Table I, the emollient employed is petrolatum. Comparative Example A contains no sodium lauryl sulfate. As can be seen from Examples 1 to 4, the addition of sodium lauryl sulfate of up to 5% improved the consistency of the cream compared to the cream composition containing no sodium lauryl sulfate (Comparative Example A) and the cream composition containing 10% sodium lauryl sulfate. The softest cream produced, having a penetration value of 185, was produced by a sodium lauryl sulfate content of 3% by weight, with the cream being somewhat harder at sodium lauryl sulfate contents below (1%) and above (5%).

TABLE I

| Example No. | A | 1 | 2 | 3 | 4 |
|---|---|---|---|---|---|
| Sodium Cocoyl Isethionate | 20 | 19 | 17 | 15 | 10 |
| Sodium Lauryl Sulfate | 0 | 1 | 3 | 5 | 10 |
| Glycerine | 50 | 50 | 50 | 50 | 50 |
| Petrolatum | 30 | 30 | 30 | 30 | 30 |
| Penetration Value (mm × 10) | 80 | 125 | 185 | 130 | 80 |

In Examples 5 to 7, the formulations of which are in Table II, the emollient employed is mineral oil, and microcrystalline wax (6%) has been added. As in evident from Table II, a 3% sodium lauryl sulfate content again produced the softest cream (penetration value 160) compared to slightly lower and slightly higher sodium lauryl sulfate contents.

TABLE II

| Example No. | B | 5 | 6 | 7 |
|---|---|---|---|---|
| Sodium cocoyl isethionate | 20 | 19 | 17 | 15 |
| Sodium lauryl sulfate | 0 | 1 | 3 | 5 |
| Mineral oil | 24 | 24 | 24 | 24 |
| Microcrystalline wax | 6 | 6 | 6 | 6 |
| Glycerine | 50 | 50 | 50 | 50 |
| Penetration Value (mm × 10) | 145 | 105 | 160 | 120 |

Examples 8 to 10 further demonstrate that a sodium lauryl sulfate content of 3% provides the softest cream, compared to lower and higher sodium lauryl sulfate levels. In Examples 8 to 10, the emollient employed is an ester; namely isopropyl palmitate. The formulations and penetration values for Examples 8 to 10 as well as Comparative Example C (containing no sodium lauryl sulfate) are presented in Table III.

TABLE III

| Example No. | C | 8 | 9 | 10 |
|---|---|---|---|---|
| Sodium cocoyl isethionate | 20 | 19 | 17 | 15 |
| Sodium lauryl sulfate | 0 | 1 | 3 | 5 |
| Isopropyl palmitate | 24 | 24 | 24 | 24 |
| Microcrystalline wax | 6 | 6 | 6 | 6 |
| Glycerine | 50 | 50 | 50 | 50 |
| Penetration value (mm × 10) | 180 | 175 | 180 | 100 |

EXAMPLES 11 TO 21

The following are specific, non-limiting, examples of compositions formed in accordance with the present invention.

EXAMPLE 11

| Ingredient | % |
|---|---|
| Sodium Cocoyl Isethionate | 12.00 |
| Sodium Lauryl Sulfate | 3.00 |
| Petrolatum (USP) | 30.00 |
| Glycerine (USP) | 55.00 |

EXAMPLE 12

| Ingredient | % |
|---|---|
| Sodium Cocoyl Isethionate | 12.00 |
| Sodium Lauryl Sulfate | 3.00 |
| Petrolatum (USP) | 25.00 |
| Glycerine | 59.95 |
| Xanthan Gum | 0.05 |

EXAMPLE 13

| Ingredient | % |
|---|---|
| Sodium Cocoyl Isethionate | 12.00 |
| Sodium Lauryl Sulfate | 2.00 |
| Sodium Lauryl Sulfoacetate | 1.00 |
| Petrolatum (USP) | 30.00 |
| Glycerine | 55.00 |

EXAMPLE 14

| Ingredient | % |
|---|---|
| Sodium Cocoyl Isethionate | 12.00 |
| Sodium Lauryl Sulfate | 3.00 |
| Petrolatum (USP) | 30.00 |

-continued

| Ingredient | % |
| --- | --- |
| Potassium Polymetaphosphate | 0.50 |
| Glycerine | 54.00 |
| Perfume | 0.50 |

EXAMPLE 15

| Ingredient | % |
| --- | --- |
| Sodium Cocoyl Isethionate | 16.00 |
| Sodium Lauryl Sulfate | 3.00 |
| Petrolatum (USP) | 25.00 |
| Glycerine | 54.00 |

EXAMPLE 16

| Ingredient | % |
| --- | --- |
| Sodium Cocoyl Isethionate | 12.00 |
| Sodium Lauryl Sulfate | 3.00 |
| Petrolatum | 27.00 |
| $C_{12-15}$ Alcohol Benzoate | 3.00 |
| Glycerine | 55.00 |

EXAMPLE 17

| Ingredient | % |
| --- | --- |
| Sodium Cocoyl Isethionate | 12.00 |
| Sodium Lauryl Sulfate | 3.00 |
| Petrolatum | 25.00 |
| Mineral Oil | 5.00 |
| N-Pentane | 5.00 |
| Glycerine | 50.00 |

EXAMPLE 18

| Ingredient | % |
| --- | --- |
| Sodium Cocoyl Isethionate | 12.00 |
| Sodium Lauryl Sulfate | 3.00 |
| Mineral Oil | 20.00 |
| Micro Crystalline Wax | 10.00 |
| Glycerine | 55.00 |

EXAMPLE 19

| Ingredient | % |
| --- | --- |
| Sodium Cocoyl Isethionate | 12.00 |
| Sodium Lauryl Sulfate | 3.00 |
| Isopropyl Palmitate | 24.00 |
| Micro Crystalline Wax | 6.00 |
| Glycerine | 55.00 |

EXAMPLE 20

| Ingredient | % |
| --- | --- |
| Sodium Cocoyl Isethionate | 12.00 |
| Sodium Lauryl Sulfate | 3.00 |
| Petrolatum (USP) | 30.00 |
| Dimethicone | 2.00 |
| Mineral Oil | 2.00 |
| Perfume | 0.30 |

-continued

| Ingredient | % |
| --- | --- |
| Glycerine | 50.70 |

EXAMPLE 21

| Ingredient | % |
| --- | --- |
| Sodium Cocoyl Isethionate | 10.00 |
| Sodium Lauryl Sulfoacetate | 2.00 |
| Sodium Lauryl Sulfate | 3.00 |
| Petrolatum (USP) | 30.00 |
| Mineral Oil | 3.00 |
| Perfume | 0.30 |
| Glycerine | 51.70 |

We claim:

1. An anhydrous cream composition comprising
   a) glycerin in an amount from about 40 to about 60% by weight based on the weight of the total composition;
   b) sodium cocoyl isethionate in an amount from about 10 to about 19% by weight based on the weight of the total composition;
   c) emollients in an amount from about 10 to about 40% by weight based on the weight of the total composition; and
   d) sodium lauryl sulfate in an amount from about 1 to about 5% by weight based on the weight of the total composition.

2. An anhydrous cream composition as in claim 1 further comprising microcrystalline wax.

3. A composition as in claim 2 wherein said microcrystalline wax is present in an amount from about 4 to 10% by weight based on the total weight of the composition.

4. A composition as in claim 1 wherein said emollients are selected from the group consisting of petrolatum, mineral oils, and esters.

5. A composition as in claim 4 wherein said emollient is an ester selected from the group consisting of isopropyl palmitate, isopropyl myristate and $C_{12}-C_{15}$ alcohol benzoates.

6. A composition as in claim 1 further comprising a foam booster.

7. A composition as in claim 6 wherein said foam booster is selected from the group consisting of potassium polymetaphosphate, n-pentane, isopentane, sodium lauryl sulfate actetate, amides and sarcosynates.

8. A composition as in claim 6 wherein said foam booster is present in an amount up to about 5% by weight based on the weight of the total composition.

9. A composition as in claim 1 further comprising a pharmaceutically effective amount of an active ingredient.

10. A composition as in claim 9 wherein said active ingredient is selected from the group consisting of deodorants, medicaments and antibacterial agents.

11. a composition as in claim 9 wherein said active ingredient is selected from the group consisting of coal tar, benzoyl peroxide, vitamin A, vitamin E, triclosan, PVP-Iodine and salicylic acid.

12. A composition as in claim 1 wherein sodium lauryl sulfate is present in an amount of about 3% by weight of the total composition.

13. A composition as in claim 1 wherein the ratio of sodium lauryl sulfate to sodium cocoyl isethionate is in the range of about 1:3 to about 1:6.

* * * * *